United States Patent
Yokomizo et al.

(10) Patent No.: US 8,851,296 B2
(45) Date of Patent: Oct. 7, 2014

(54) BLOOD PROCESSING FILTER AND THE METHOD FOR MANUFACTURING THE SAME

(75) Inventors: Tomohisa Yokomizo, Tokyo (JP); Morikazu Miura, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 266 days.

(21) Appl. No.: 13/237,061

(22) Filed: Sep. 20, 2011

(65) Prior Publication Data

US 2012/0067811 A1     Mar. 22, 2012

Related U.S. Application Data

(60) Provisional application No. 61/384,904, filed on Sep. 21, 2010.

(51) Int. Cl.
| | |
|---|---|
| *B01D 35/00* | (2006.01) |
| *B01D 37/00* | (2006.01) |
| *A61M 1/36* | (2006.01) |
| *A61M 1/02* | (2006.01) |
| *B01D 29/05* | (2006.01) |

(52) U.S. Cl.
CPC ............... *A61M 1/02* (2013.01); *A61M 1/3636* (2013.01); *A61M 2202/0439* (2013.01)
USPC ............................ 210/450; 210/767; 210/435

(58) Field of Classification Search
USPC ......... 210/450, 337, 767, 645, 782, 435, 650, 210/232, 445, 453, 461, 483
See application file for complete search history.

(56) References Cited

U.S. PATENT DOCUMENTS

| 7,445,124 B2 | 11/2008 | Cavallini et al. | |
|---|---|---|---|
| 7,641,794 B2 * | 1/2010 | Oka et al. | 210/259 |
| 2003/0209479 A1 * | 11/2003 | Lynn et al. | 210/257.1 |
| 2004/0251195 A1 * | 12/2004 | Oka et al. | 210/489 |

(Continued)

FOREIGN PATENT DOCUMENTS

| EP | 0526678 | 12/1991 |
|---|---|---|
| JP | 1-320064 | 12/1989 |

(Continued)

OTHER PUBLICATIONS

Machine translation of JP2007253374.*

(Continued)

*Primary Examiner* — Nam Nguyen
*Assistant Examiner* — Madeline Gonzalez
(74) *Attorney, Agent, or Firm* — Greenblum & Bernstein, P.L.C.

(57) ABSTRACT

This invention relates to a blood processing filter including a band-shaped first seal part that seals an inlet-side flexible container of the blood processing filter and a filter element of the blood processing filter so as to surround an inlet port, and an annular second seal part that seals at least the inlet-side flexible container and an outlet-side flexible container and is formed surrounding the first seal part at a position that is closer to an outer edge than the first seal part. A valley part corresponding to the first seal part is provided on an outlet side of the filter element. An outlet opening that communicates with an inside of the outlet-side flexible container is formed in the outlet port. At least one portion of the outlet opening is arranged so as to overlap with the valley part.

6 Claims, 9 Drawing Sheets

(56) References Cited

U.S. PATENT DOCUMENTS

| | | | |
|---|---|---|---|
| 2012/0067810 A1* | 3/2012 | Yokomizo et al. | 210/450 |
| 2012/0160763 A1* | 6/2012 | Yokomizo et al. | 210/435 |
| 2012/0160782 A1* | 6/2012 | Yokomizo et al. | 210/767 |

FOREIGN PATENT DOCUMENTS

| | | | |
|---|---|---|---|
| JP | 7-267871 | | 10/1995 |
| JP | 11-216179 | | 8/1998 |
| JP | 2006-507881 | | 3/2006 |
| JP | 2007253374 | * | 4/2007 |
| JP | 2008-86352 | | 4/2008 |
| JP | 2011-72814 | | 4/2011 |
| WO | 90/15660 | | 12/1990 |
| WO | 92/20428 | | 11/1992 |
| WO | 95/17236 | | 6/1995 |
| WO | 01/91880 | | 12/2001 |
| WO | 02/04045 | | 1/2002 |
| WO | 2004/050147 | | 6/2004 |

OTHER PUBLICATIONS

U.S. Appl. No. 13/237,029 to Tomohisa Yokomizo et al., filed Sep. 20, 2011.
International Preliminary Report on Patentability for PCT/JP2011/071396, mailed Apr. 16, 2013.
Search report from P.C.T., mail date is Nov. 22, 2011.

* cited by examiner

BLOOD PROCESSING FILTER AND THE METHOD FOR MANUFACTURING THE SAME

BACKGROUND OF THE INVENTION

1. Field of the Invention

The present invention relates to a blood processing filter for removing undesirable components such as aggregates and leukocytes from blood. In particular, the present invention relates to a precise and disposable blood processing filter for removing microaggregates and leukocytes which may cause side effects from whole blood preparations, erythrocyte preparations, thrombocyte preparations, blood plasma preparations and the like for blood transfusion, as well as a method for manufacturing the blood processing filter.

2. Related Background Art

It is becoming common for whole blood collected from a donor to be separated into blood component preparations such as an erythrocyte preparation, a thrombocyte preparation, and a blood plasma preparation and stored for transfusion. Since microaggregates and leukocytes included in these blood preparations cause various side effects during blood transfusion, the number of occasions for removing these undesirable components before blood transfusion has been increasing. The need for leukocyte removal has widely been recognized particularly in recent years. Legislation regarding removal of leukocytes from all kinds of blood preparations for blood transfusion before being used for transfusion has been introduced in an increasing number of countries.

The most common method of removing leukocytes from blood preparations is by processing blood preparations using a leukocyte removal filter. Conventionally, in many cases blood preparations processed using a leukocyte removal filter have been processed at the bedside when blood transfusion is performed. In recent years, however, to improve quality control of leukocyte-free preparations and efficiency of leukocyte removal operations, it is more common, particularly in developed countries, to process the blood preparations in blood centers before storing the blood preparations (pre-storage leukocyte removal).

A blood collection-separation set, typically consisting of two to four flexible bags, a tube connecting these bags, an anticoagulant, an erythrocyte preservation solution, a blood collection needle, and the like has been used for collecting blood from a donor, separating the blood into several blood components, and storing the blood components. A system in which a leukocyte removal filter is incorporated into such a blood collection-separation set has been widely used as an optimum system for the above-mentioned "pre-storage leukocyte removal". Such a system is called a "closed system" or an "integrated system" or the like. Such systems are disclosed in Japanese Patent Laid-Open No. 1-320064, International Publication No. WO 92/020428 and the like.

Conventionally, a filter element made from nonwoven fabric or a porous body packed in a hard container of polycarbonate or the like has been widely used as a leukocyte removal filter. However, because the container used in such a filter has a low level of air permeability, there is the problem that it is difficult to apply steam sterilization, which is widely used as a sterilization process in blood collection-separation sets. In one type of closed system, leukocytes are first removed from the whole blood preparation after collecting the blood. Subsequently, after the leukocyte removal filter is separated, the leukocyte-fee blood is centrifuged for separation into various components. In another type of closed system, the whole blood is first centrifuged to be divided into various blood components, and then the leukocytes are removed. In the latter system, the leukocyte removal filter is also centrifuged together with the blood collection-separation set. At such time, a hard container may damage bags and tubes, or the hard container itself may not withstand the stress and may break during centrifugation.

To solve these problems, flexible leukocyte removal filters have been developed in which the container is made of a material having excellent flexibility and steam permeability that is the same as or similar to the material used for the bags of the blood collection-separation set. These flexible leukocyte removal filters that use a container made of a material having excellent flexibility and steam permeability are broadly classified into a type in which the filter element is welded to a sheet-like flexible frame, which is then welded to a housing material (see European Patent Specification EP 0526678 and Japanese Patent Laid-Open No. 11-216179), and a type in which a flexible container is directly welded to the filter element (see Japanese Patent Laid-Open No. 7-267871 and International Publication No. WO 95/17236). The former type may be hereinafter referred to as "frame welding type" and the latter may be referred to as "container welding type".

Normally, when processing blood with these types of leukocyte removal filters, a bag containing a blood preparation to be processed that is connected to a blood inlet side of the filter via a tube is placed at a height that is approximately 20 to 100 cm higher than the filter to allow the blood preparation to pass through the filter by the action of gravity. After filtration, the blood preparation is stored in a recovery bag that is connected to a blood outlet side of the filter via a tube. During filtration, a pressure loss occurs due to the resistance of the filter element, whereby the pressure in a space on the inlet side of the filter becomes a positive pressure. In the case of the filter that includes a flexible container, there is a tendency for the flexibility of the container itself to cause the container to swell like a balloon due to the positive pressure, thereby pressing the filter element against the container on the outlet side.

Furthermore, normally, a bag for storing blood that has been processed with the blood filter is placed at a position that is 50 to 100 cm lower than the filter, and blood moves through a channel on the downstream side due to the action of gravity. Hence, there is a tendency for the outlet side of the filter to become a negative pressure due to this action, and the flexible container is liable to adhere to the filter element.

That is, it has been pointed out previously that in the case of a filter that uses a flexible container, there is a problem that there is a strong tendency for the filter element to adhere to the outlet-side container due to a dual force, and as a result the flow of blood is obstructed and an adequate flow rate can not be obtained.

Various measures have been proposed to solve this problem. Representative examples of such measures include a method that inserts a soft polyvinyl chloride tube referred to as a "connecting rod" between the filter element and the outlet-side container to prevent adherence (see European Patent Specification EP 0526678), a method that prevents adherence by providing concavities and convexities with vertical intervals of 0.2 mm to 2 mm on the internal surface of a soft container (Japanese Patent Laid-Open No. 11-216179), and a method that inserts a screen made of knit fiber (International Publication No. WO 95/17236).

However, in a case in which a separate member such as a connecting rod or a screen is inserted, because it is required to perform welding precisely when welding the separate member to the container, there are the problems that a welding defect may occur, the manufacturing process, is complicated, and the manufacturing cost is increased by the use of additional materials.

Furthermore, in the case of providing concavities and convexities on the internal surface of a container, there is the problem that the concavities and convexities on the internal surface of the container may induce a welding defect or may decrease the pressure resistance when the container material and the filter element are welded together.

Further, in a filter in which at least one of an inlet and an outlet is straddled and sealed by a second seal part, as disclosed in European Patent Specification EP 0526678, Japanese Patent Laid-Open No. 11-216179, and International Publication No. WO 04/050147, it is necessary to use a complicated tool or process used for sealing.

As described above, when the conventional technology is investigated from the point of view of a disadvantage caused by negative pressure that arises on the filter outlet side, in other words, from the point of view of how to secure a space that can serve as a passage for blood to pass through between the container and the filter element that are attempting to adhere to each other, it is found that the conventional technology is not necessarily satisfactory.

SUMMARY OF THE INVENTION

An object of the present invention is to provide a blood processing filter that, without leading to a risk of a welding defect, complicating the manufacturing process, or increasing costs, can avoid a situation in which a flow is inhibited and filtering performance is lowered due to adherence or the like between an outlet-side container and a filter element of a flexible filter, can effectively utilize the entire filter element, and can simultaneously achieve a high flow rate and high filtering performance.

To solve the above described problems, the inventors of the present invention carried out studies with respect to the shapes of flexible containers, filter elements and the like of blood processing filters as well as to methods of assembling the blood processing filters, and succeeded in solving the above problems by providing a blood processing filter that can alleviate a decrease in a flow and a decline in leukocyte removal performance that are caused by adherence between an outlet-side container and a filter element that arises as a result of a negative pressure on a filter outlet side.

Specifically, the present invention relates to a blood processing filter including a sheet-like filter element, an inlet-side flexible container and an outlet-side flexible container that sandwich the filter element and are sealed thereto, an inlet port provided in the inlet-side flexible container for accepting blood before being processed by the filter element, and an outlet port provided in the outlet-side flexible container for discharging blood after being processed by the filter element; the blood processing filter further including: a band-shaped first seal part that seals the inlet-side flexible container and the filter element so as to surround the inlet port; and an annular second seal part that seals at least the inlet-side flexible container and the outlet-side flexible container and that is formed so as to surround the first seal part at a position that is closer to an outer edge than the first seal part; wherein: a valley part corresponding to the first seal part is provided on an outlet side of the filter element; an outlet opening that communicates with an inside of the outlet-side flexible container is formed in the outlet port; and at least one portion of the outlet opening is arranged so as to overlap with the valley part. In this connection, in the present invention the term "blood" includes blood preparations such as whole blood preparations, erythrocyte preparations, thrombocyte preparations, and blood plasma preparations for blood transfusion.

According to the above described blood processing filter, even if a dual force that is caused by a positive pressure on the inlet side and a negative pressure on the outlet side acts when filtering, a gap is produced between the filter element and the outlet-side flexible container by the valley part that is formed on the outlet side of the filter element, and the flow of blood is ensured by the gap. Further, since at least one portion of the outlet opening of the outlet port is arranged so as to overlap with the valley part, a blood flow channel of the valley part and the outlet port are in a connected state, and thus blood can be efficiently discharged to outside, and at the same time, a risk of the outlet opening being blocked by the filter element can be eliminated. Accordingly, a situation in which a flow is inhibited and filtering performance is lowered due to adherence or the like between the outlet-side flexible container and the filter element of the blood processing filter is avoided and the configuration is advantageous in terms of effectively utilizing the entire filter element, and thus both a high filtering flow rate and high filtering performance can be achieved in a compatible manner.

The present invention can also provide a blood processing filter according to the above described blood processing filter, in which an inlet opening that communicates with an inside of the inlet-side flexible container is formed in the inlet port, and the outlet opening is provided at a position that is higher than the inlet opening in a state in which the blood processing filter is placed upright to perform blood processing.

Further, the present invention can provide a blood processing filter according to the above described blood processing filter, in which the outlet opening is provided at an uppermost position of a region that overlaps with the valley part in a state which the blood processing filter is placed upright to perform blood processing.

The present invention also relates to a method for manufacturing a blood processing filter that includes a sheet-like filter element, an inlet-side flexible container and an outlet-side flexible container that sandwich the filter element and are sealed thereto, an inlet port provided in the inlet-side flexible container for accepting blood before being processed by the filter element, and an outlet port provided in the outlet-side flexible container for discharging blood after being processed by the filter element; a first sealing step of forming a band-shaped first seal part by sealing the inlet-side flexible container and the filter element so as to surround an area where the inlet port is formed, without adhering the filter element and the outlet-side flexible container; and a second sealing step of forming an annular second seal part by sealing so as to surround the first seal part at a position that is closer to an outer edge than the first seal part; wherein: a band-shaped valley part on a rear side that corresponds to the first seal part is generated on an outlet side of the filter element by the first sealing step; an outlet opening that communicates with an inside of the outlet-side flexible container is formed in the outlet port; and at least one portion of the outlet opening is formed so as to overlap with the valley part.

The present invention can also provide a method for manufacturing a blood processing filter according to the above described method, in which an inlet opening that communicates with an inside of the inlet-side flexible container is formed in the inlet port, and the outlet opening of the outlet port is provided at a position that is higher than the inlet opening of the inlet port in a state in which the blood processing filter is placed upright to perform blood processing.

Further, the present invention can provide a method for manufacturing a blood processing filter according to the above described method, in which, the outlet opening of the outlet port is provided at an uppermost position of a region that overlaps with the valley part in a state which the blood processing filter is placed upright to perform blood processing.

DESCRIPTION OF THE PREFERRED EMBODIMENTS

Embodiments of the present invention are described hereunder with reference to the drawings. Note that the term "blood" that is described in each of the following embodiments includes blood preparations such as whole blood preparations, erythrocyte preparations, thrombocyte preparations and blood plasma preparations for blood transfusion. Further, although various forms can be adopted for the external shape of the blood processing filter, such as a rectangular shape, a disc shape, an oval disc shape, and an elliptical shape, a rectangular shape is preferable for decreasing loss of materials when the filters are manufactured. Accordingly, in the following embodiments, an example in which the blood processing filter has a rectangular shape is described.

Figure 1:
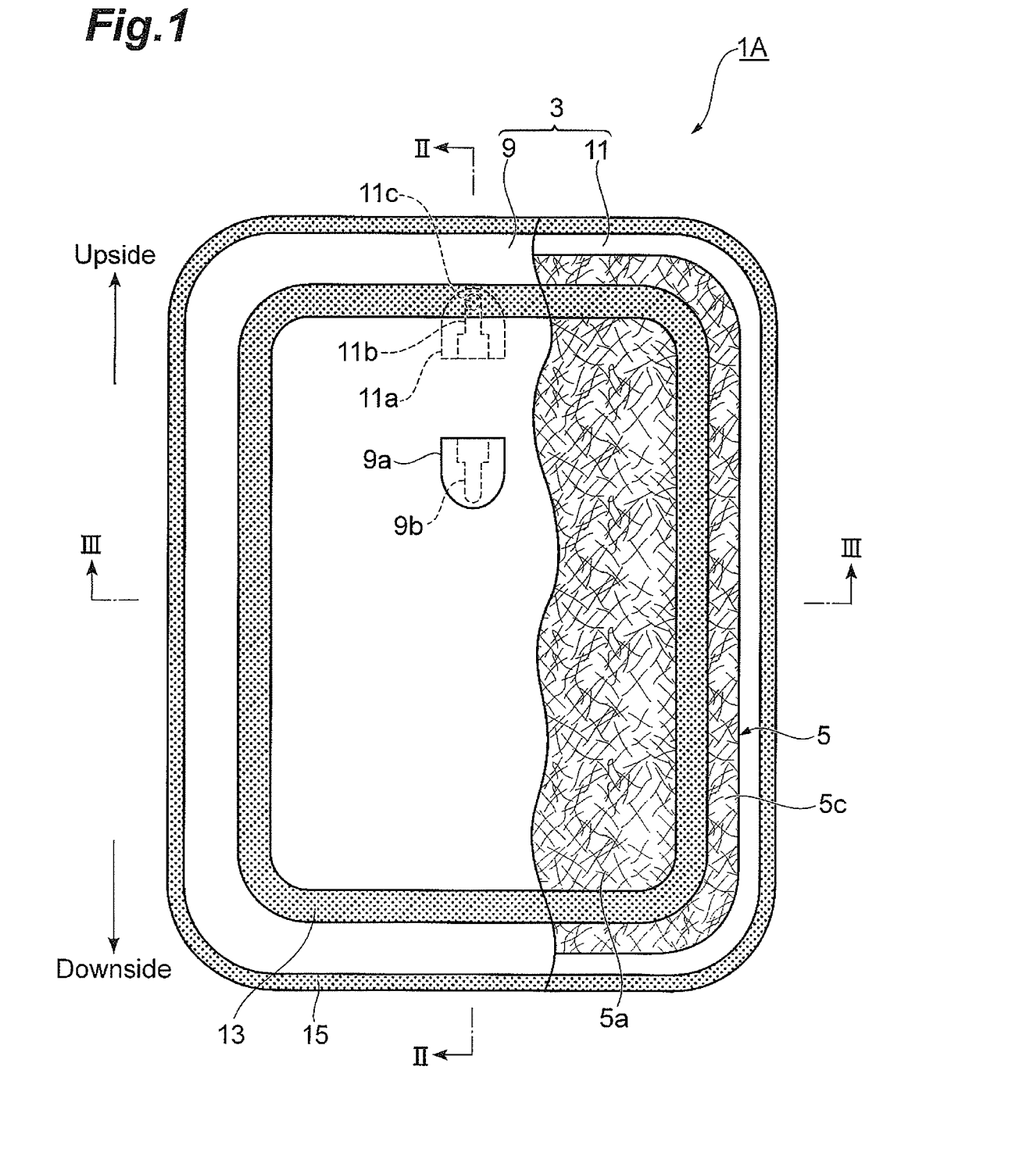
FIG. 1 is a plan view that illustrates one portion of a blood processing filter according to a first embodiment of the present invention, that is shown in a cut-away manner.
Figure 2:
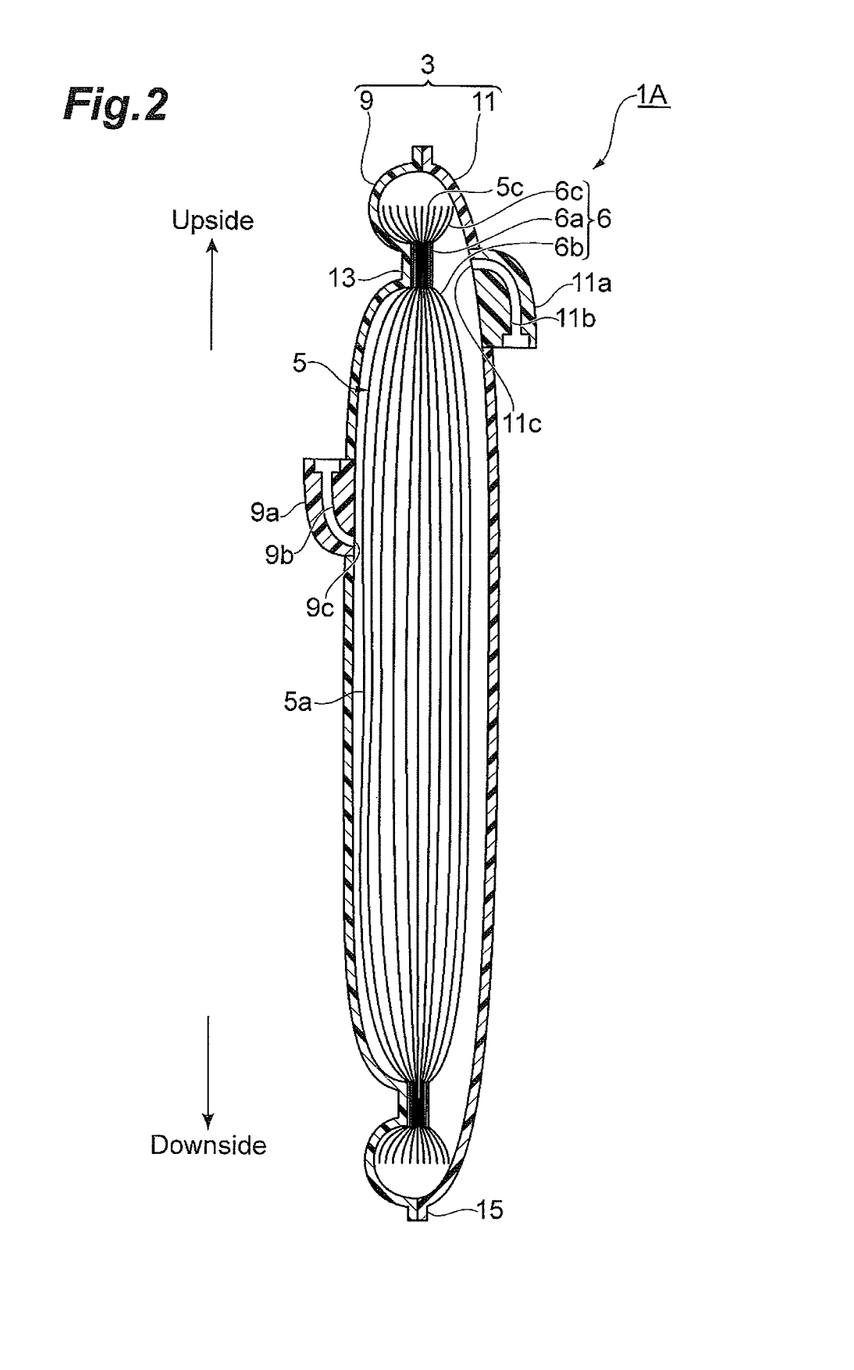
FIG. 2 is a sectional view taken along a line II-II in FIG. 1.
Figure 3:
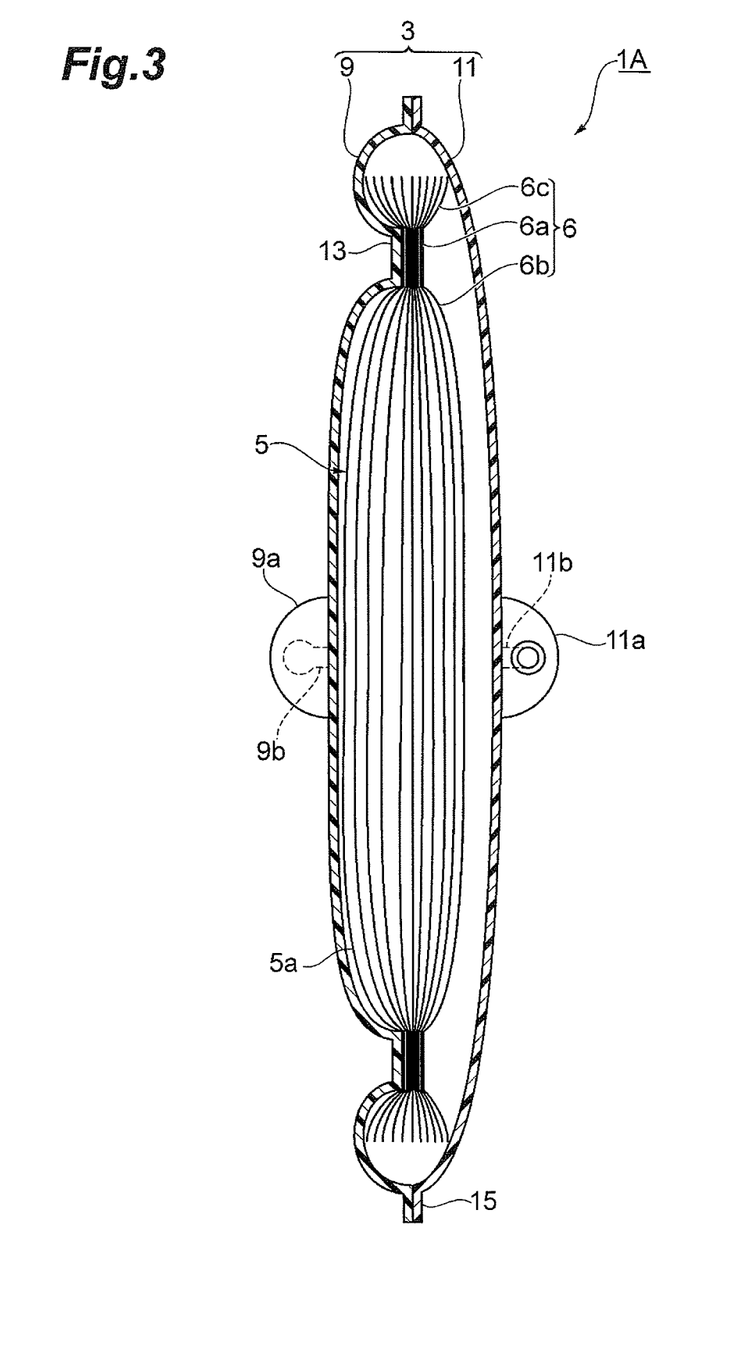
FIG. 3 is a sectional view taken along a line III-III in FIG. 1.

First, a blood processing filter 1A relating to a first embodiment of the present invention is described referring to FIGS. 1 to 3. The blood processing filter 1A includes a flexible container 3 having an inlet port 9a and an outlet port 11a for blood, and a sheet-like filter element 5 that is arranged so as to divide the inside of the flexible container 3 into an inlet port 9a side and an outlet port 11a side.

The flexible container 3 has a rectangular, flat shape. Here, the term "flat shape" means a shape having a thin thickness and a wide surface. The flexible container 3 includes an inlet-side container 9 that has a rectangular sheet shape, and an outlet-side container 11 that has a rectangular sheet shape. An inlet port 9a in which an inlet flow channel 9b that allows the inside and the outside to communicate is formed is sealed in the inlet-side container 9. An outlet port 11a in which an outlet flow channel 11b that allows the inside and the outside to communicate is formed is sealed in the outlet-side container 11. In this connection, as used herein, the term "seal (to seal)" refers to fixing by bonding (including by means of welding) to a degree that can prevent leakage of a liquid.

Further, the inlet-side container 9 is an example of an inlet-side flexible container, and the outlet-side container 11 is an example of an outlet-side flexible container.

The inlet-side container 9 and the outlet-side container 11 overlap with each other through the rectangular filter element 5. The inlet-side container 9 is sealed along the periphery of the filter element 5 in a state in which the inlet-side container 9 is adhered to the filter element 5. A band-shaped bonding region along the periphery of the filter element 5 is an inside seal part 13. The inside seal part 13 surrounds the inlet port 9a in a rectangular ring shape. An inner region that is further on the inside than the inside seal part 13 is a filtering region through which blood flows. A portion of the filter element 5 that faces the filtering region is an effective filtering portion 5a. In this connection, a protruding nonwoven fabric portion 5c that is a surplus portion of the filter element 5 protrudes to the outside of the inside seal part 13 within the flexible container 3. The inside seal part 13 corresponds to a first seal part.

Figure 4:
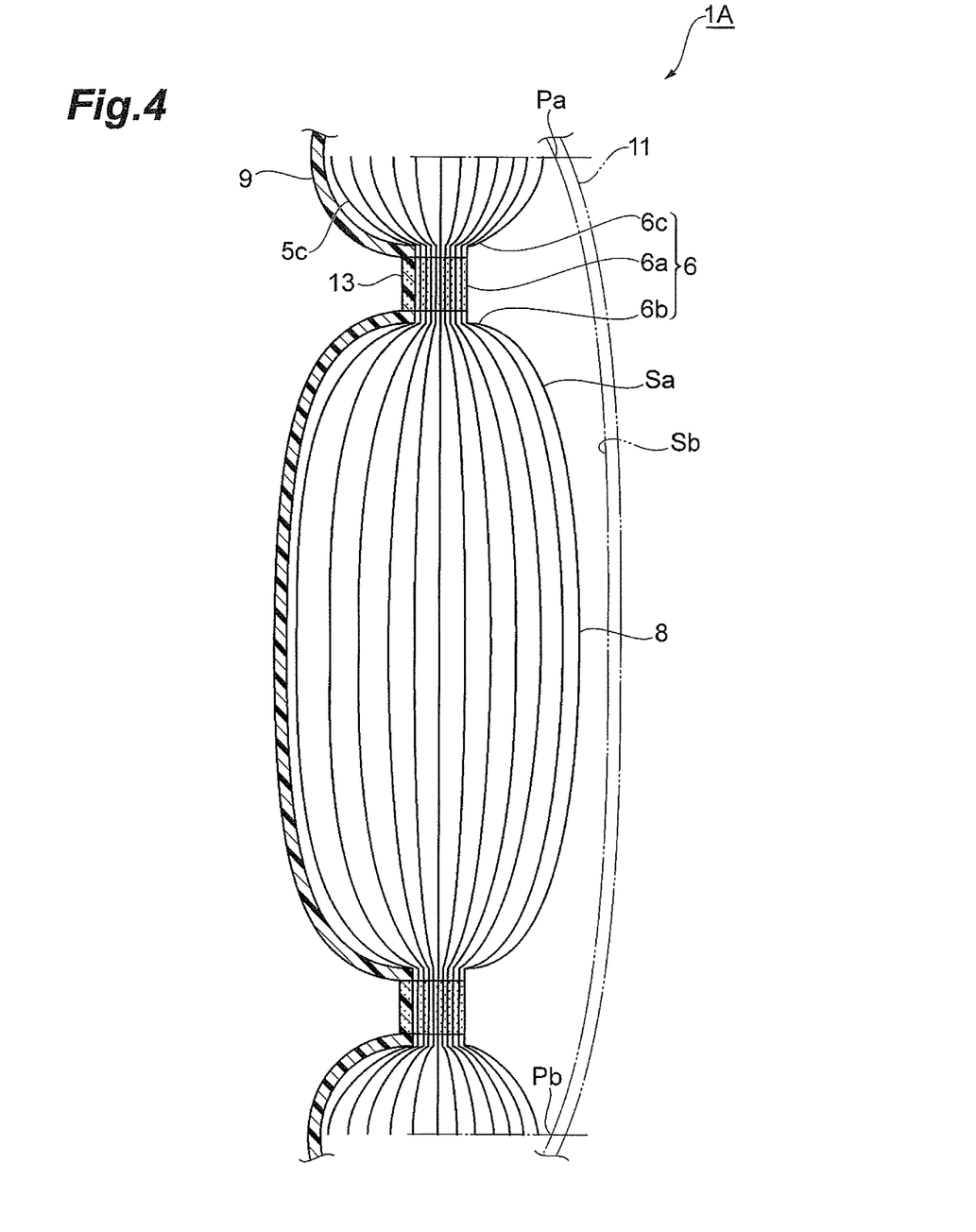
FIG. 4 is a view that schematically illustrates a relationship between a portion corresponding to a valley part of a filter element and another portion.

On the outlet side of the filter element 5, that is, on the rear side of the filter element 5, a rectangular ring shaped recess is formed in correspondence to the rectangular ring-shaped inside seal part 13 (see FIG. 4). This recess is fainted as a result of the filter element 5 being adhered to the inlet-side container 9. This recess is a valley part 6 that is provided on the outlet side of the filter element 5.

The peripheries of the inlet-side container 9 and the outlet-side container 11 are sealed together in a mutually overlapping manner so as to surround the inside seal part 13 in a ring shape at a position that is closer to an outer edge than the inside seal part 13. The band-shaped bonding region in which the inlet-side container 9 and the outlet-side container 11 are directly bonded is an outside seal part 15. The outside seal part 15 corresponds to a second seal part.

The outlet-side container 11 is not bonded to the filter element 5. In an at-rest state, the outlet-side container 11 is in a state in which the outlet-side container 11 is roughly separated from the valley part 6 of the filter element 5. If a state is assumed in which blood is flowing (a negative pressure state), an empty space region (hereunder, referred to as a "passage region") S is formed between the filter element 5 and the outlet-side container 11 by the valley part 6 of the filter element 5 (see FIG. 6).

The valley part 6 of the filter element 5 will now be described in further detail referring to FIG. 4. FIG. 4 is a schematic view that illustrates the filter element 5 in an at-rest state, that is, a state in which blood is not flowing. In particular, FIG. 4 is a view that schematically illustrates the relationship between an area in which the valley part 6 is foamed and other areas. The valley part 6 includes a bottom part 6a that overlaps with the inside seal part 13, an inner slanted face portion 6b that rises towards the inside of the inside seal part 13 from the bottom part 6a, and an outer slanted face portion 6c that rises towards the outside of the inside seal part 13. The inner slanted face portion 6b smoothly connects to a main region portion 8 on the outlet side of the filter element 5. The outer slanted face portion 6c is a region that is formed by the protruding nonwoven fabric portion 5c.

Formation of the valley part 6 will now be described in detail. A laminated filter element has a constant thickness, and the surface of the filter element is in a flat state when a process such as welding has not been performed. Subsequently, for example, if the two faces of the filter element are sandwiched with a PVC sheet and high frequency welding is performed, the welded place is crushed in the welding process, and the welded place becomes thin in comparison to the original thickness of the filter element. In this case, according to the filter element 5 of the present embodiment, for example, high frequency welding is carried out using a predetermined mold to form the inside seal part 13, and as a result an annular welded place is formed. Although the places other than the welded place are substantially flat over the entire area of the filter element 5 after welding also, only the vicinity of the welded place is different, and when attention is focused on the outlet side it can be seen that a place adjoining the welded place rises almost perpendicularly from the welded place and connects to a flat portion (main region portion 8) of the filter element 5. More specifically, the region corresponding to the welded place is the bottom part 6a of the valley part 6, the region that rises almost perpendicularly towards the inner side from the bottom part 6a is the inner slanted face portion 6b, and the region that rises almost perpendicularly towards the outer side from the bottom part 6a is the outer slanted face portion 6c.

Next, the relationship between a face on the outlet side of the filter element 5 on which the valley part 6 is formed (hereunder, referred to as "outlet-side nonwoven fabric surface") and the outlet-side container 11 is described. First, a cross section (hereunder, referred to as "hypothetical cross section") that cuts the blood processing filter 1A along an arbitrary straight line that passes through approximately the center of the outlet-side nonwoven fabric surface is supposed. FIG. 4 is a view that schematically illustrates the hypothetical cross section.

In this case, a first line segment Sa that indicates the outlet-side nonwoven fabric surface on the hypothetical cross section, and a second line segment Sb that indicates a region which corresponds to the outlet-side nonwoven fabric surface among the entire inner surface of the outlet-side container 11 on the hypothetical cross section are specified. The first line segment Sa links both ends of the outlet-side nonwoven fabric surface and is formed in the same shape as the outlet-side nonwoven fabric surface. With respect to the second line segment Sb, first, an orthogonal direction to the longitudinal direction of the filter element 5 on the hypothetical cross section is assumed to be a corresponding direction, and a straight line that extends along the respective corresponding directions from both ends of the outlet-side nonwoven fabric surface is assumed. Next, two points Pa and Pb at which the two straight lines intersect with the inner surface of the outlet-side container 11 are specified. The two points Pa and Pb correspond to both ends of the outlet-side nonwoven fabric surface on the inner surface of the outlet-side container 11. A line segment that links the two points Pa and Pb in a manner that follows the shape of the inner surface of the outlet-side container 11 is the second line segment Sb.

Comparing the first line segment Sa and the second line segment Sb, since the valley part 6 is formed in the filter element 5, the first line segment Sa is longer than the second line segment Sb. As a result an empty space region is formed in the valley part 6 in an at-rest state. Further, with respect to the outlet-side container 11, although the material thereof has some margin for expansion and contraction it is not a material that expands by any amount, and since the first line segment Sa is longer than the second line segment Sb, even if a state is entered in which blood flows and is attached thereto (is attached due to a negative pressure), the outlet-side container 11 does not contact the filter element 5 in the vicinity of the inside seal part 13, in particular in the vicinity of the bottom part 6a of the valley part 6. As a result, the passage region S is formed which can be used as a flow channel for blood (see FIG. 6).

As shown in FIG. 1 to FIG. 3, the inlet port 9a that is sealed in the inlet-side container 9 can be appropriately arranged in a region on the inside of the inside seal part 13. The inlet port 9a according to the present embodiment is arranged at one end side in the longitudinal direction of the flexible container 3, that is, on the upper side in a state in which the blood processing filter 1A is placed upright for blood processing. An inlet flow channel 9b that accepts pre-processing blood when an inlet-side circuit 102 (see FIG. 5) through which blood flows is formed, is formed in the inlet port 9a. An inlet opening 9c is fainted in the inlet port 9a. The inlet opening 9c allows the inlet flow channel 9b and the inside of the inlet-side container 9 to communicate.

The outlet port 11a that is sealed in the outlet-side container 11 is arranged in a region on the inside of the outside seal part 15. An outlet flow channel 11b that discharges blood that is processed by the filter element 5 when an outlet-side circuit 104 (see FIG. 5) through which blood flows is formed, is formed in the outlet port 11a.

An outlet opening 11c is formed in the outlet port 11a. The outlet opening 11c allows the inside of the outlet-side container 11 and the outlet flow channel 11b to communicate. At least one portion of the outlet opening 11e of the outlet port 11a is arranged so as to overlap in a planar view with the valley part 6 of the filter element 5. Further, the outlet opening 11c is provided at a position that is higher than the position of the inlet opening 9c of the inlet port 9a in a state in which the blood processing filter 1A is placed upright to perform blood processing. In particular, the outlet opening 11c is provided at a position that overlaps with one portion of an uppermost side in a region that overlaps with the valley part 6.

Figure 7:
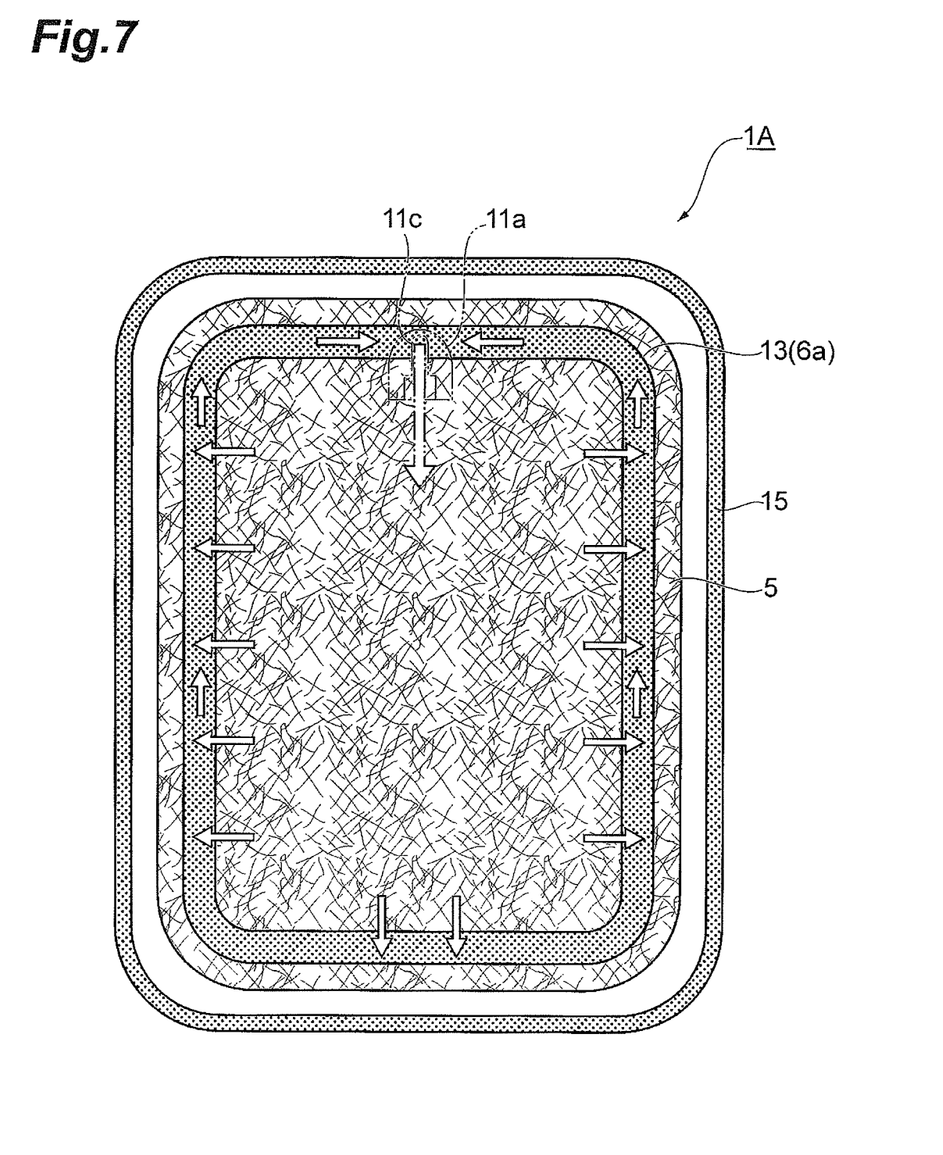
FIG. 7 is a view that schematically illustrates a flow of blood inside an outlet-side flexible container.

According to the blood processing filter 1A of the present embodiment, the outlet-side container 11 is not included in the inside seal part 13. Therefore, since the passage region S is formed by the valley part 6 of the filter element 5, it is possible to prevent a situation in which the filter element 5 in the vicinity of the inside seal part 13 is pinched by the outlet-side container 11 and a flow is inhibited. Moreover, since the valley part 6 corresponding to the inside seal part 13 is connected in a rectangular ring shape, the valley part 6 can be utilized as a passage for blood to pass through between the filter element 5 and the outlet-side container 11 (see FIG. 7).

That is, it is possible to efficiently utilize the filter material at a peripheral portion of the filter element 5 in the vicinity of the inside seal part 13, at which, in a conventional blood processing filter, blood tends to flow with difficulty. At that time, since the inside seal part 13 is positioned at the periphery of the effective filtering portion 5a of the filter element 5, a flow towards the outlet port 11a between the filter element 5 and the outlet-side container 11 is in a direction that spreads out to the surrounding area from the center of the filter material, and is the opposite to a flow in which blood converges towards the center, such as in a case where the outlet port is arranged on the inner side of the inside seal part, and it is therefore difficult for the flow of blood to be inhibited.

Further, the outlet opening 11c according to the present embodiment is provided at a position that is higher than the inlet opening 9c, and further, is the uppermost position in the region that overlaps with the valley part 6.

In the region that overlaps with the valley part 6 of the filter element 5, an area that is the uppermost portion when performing filtration by means of a gravity drop difference is a portion with the comparatively lowest pressure between the filter element 5 and the outlet-side container 11. More specifically, when the outlet port 11a (outlet opening 11c) is arranged at the uppermost position in the region that overlaps with the valley part 6, the pressure between the filter element 5 and the outlet-side container 11 can be made comparatively high at an area that is the lowermost portion when performing filtration by means of a gravity drop difference that is at a distant position from the outlet opening 11c. Accordingly, a favorable blood flow and effective utilization of the filter material can also be achieved at a portion located at a distant position from the outlet port 11a, which is a portion at which the filter material is not effectively utilized according to the conventional technology.

By arranging the outlet opening 11c and the outlet port 11a in the above described manner, the blood processing filter 1A fills with blood from the bottom upwards at a time of priming at the start of blood processing. As a result, since air can easily exit from the outlet port 11a that is arranged at the upper part of the blood processing filter 1A, more complete priming and air removal can be performed without the need to pay special attention to a gravity drop setting or a flow rate at the time of priming. Thus, the filter element 5 can be utilized more effectively as a filter material, and a higher flow rate and higher filtering performance can be obtained. At such time, since the entire blood processing filter 1A swells because blood does not flow to outside the blood processing filter 1A until priming is completed, at first glance it seems that priming of the blood processing filter 1A requires time. However, in fact, after priming ends the blood accumulated on the outlet side is discharged to outside of the blood processing filter 1A at one time by the force of gravity, and since the filter material is utilized more effectively by the more complete priming, the overall time required for the entire blood processing can be shortened.

Next, forms of the material and shape and the like of each element constituting the blood processing filter 1A are described. As described in the foregoing, the flexible container 3 is formed by the inlet-side container 9 and the outlet-side container 11. Any material that is commercially available as a sheet or a film can be used as a flexible resin that is used for the flexible container 3. For example, thermoplastic elastomers such as soft polyvinyl chloride, polyurethane, ethylene-vinyl acetate copolymer, polyolefin such as polyethylene and polypropylene, hydrogenated styrene-butadiene-styrene copolymer, styrene-isoprene-styrene copolymer, and hydrogenated products thereof, mixtures of the thermoplastic elastomer and a softening agent such as polyolefin and ethylene-ethyl acrylate, and the like may be mentioned as favorable materials. Since it can be considered that the material will contact with blood, preferable materials are soft polyvinyl chloride, polyurethane, and polyolefin that are used as the material of medical products such as blood bags, as well as thermoplastic elastomers containing these materials as main components, and more preferably the material is soft polyvinyl chloride.

Further, for example, a container described in Japanese Patent Laid-Open No. 7-267871 or a container described in International Publication No. WO 95/017236 can also be used as the flexible container 3.

The filter element 5 is manufactured using a filter material constituted by a fibrous integrated body such as nonwoven fabric or woven fabric or by a porous body such as sponge. The filter element 5 according to the present embodiment may be coated with a hydrophilic polymer to make it easier for blood to wet the filter material. Further, to facilitate attachment of leukocytes to the filter element 5 when using the blood processing filter 1A to remove leukocytes from blood, a filter material that is coated with a polymer may be used.

Next, a method for manufacturing the blood processing filter 1A according to the present embodiment is described. According to this manufacturing method, for example, the inlet-side container 9 in which the inlet port 9a has been sealed at a predetermined position, the outlet-side container 11 in which the outlet port 11a has been sealed at a predetermined position, and the filter element 5 are prepared, and an installing step is performed in which the inlet-side container 9 and the outlet-side container 11 are arranged so as to sandwich the filter element 5.

In this case, the outlet port 11a is provided so that, after manufacture of the blood processing filter 1A is completed, at least one portion of the outlet opening 11c overlaps with the valley part 6. Further, the inlet opening 9c that communicates with an inside of the inlet-side container 9 is formed in the inlet port 9a, and the outlet opening 11c is provided at a position that, after manufacture of the blood processing filter 1A is completed, is higher than the inlet opening 9c in a state in which the blood processing filter 1A is placed upright to perform blood processing. Furthermore, with respect to the region that overlaps with the valley part 6, the outlet opening 11c is provided at a position therein that, after manufacture of the blood processing filter 1A is completed, is the uppermost position in a state in which the blood processing filter 1A is placed upright to perform blood processing.

After the installing step, a first sealing step and a second sealing step are performed. In the first sealing step, the inside seal part 13 is formed by sealing the inlet-side container 9 and the filter element 5 in a band shape so as to surround the area where the inlet port 9a is formed, without adhering the filter element 5 and the outlet-side container 11. In the second sealing step, the annular outside seal part (second seal part) 15 is formed by sealing so as to surround the inside seal part 13, at a position that is closer to an outer edge than the inside seal part (first seal part) 13.

In the first sealing step, the valley part 6 that has a band shape that corresponds to the inside seal part 13 is generated on the outlet side of the filter element 5. The passage region S is formed between the outlet-side container 11 and the filter element 5 by the valley part 6.

Although formation of the inside seal part 13 in the first sealing step, more specifically, sealing of the inlet-side container 9, and the filter element 5 can be performed utilizing high frequency welding, the present invention is not limited thereto, and any kind of bonding technique, such as ultrasonic welding or thermal welding, can be used.

Likewise, although formation of the outside seal part 15 in the second sealing step, more specifically, sealing of the inlet-side container 9 and the outlet-side container 11 can be performed utilizing high frequency welding, the present invention is not limited thereto, and any kind of bonding technique, such as ultrasonic welding or thermal welding, can be used.

According to the above described manufacturing method, a form is described in which the inlet port 9a and the outlet port 11a are previously sealed to the flexible container 3. However, sealing may be performed after forming the inside seal part 13 or the outside seal part 15, or may be performed during the process of forming the inside seal part 13 or the outside seal part 15. Further, a method of sealing the inlet port 9a as a blood inlet and the outlet port 11a as a blood outlet to the flexible container 3 is not limited to high frequency welding, and any kind of bonding technique, such as thermal welding, can be used. Similarly to the flexible container 3, various known materials can be used as the material of the inlet port 9a and the outlet port 11a.

According to the above described manufacturing method, since the outlet-side container 11 is not included in the inside seal part 13, that is, since the outlet-side container 11 is not sealed to the filter element 5, there is the advantage that arrangement of the outlet port 11a in the step of sealing the outlet port 11a to the outlet-side container 11 can be performed with a comparatively high degree of freedom. More specifically, although sealing the inlet port 9a or the outlet port 11a inside the flexible container 3 is an advantage of the process of manufacturing the container welding type blood processing filter 1A in which forming the inside seal part 13 or the outside seal part 15 by a simple step is a feature, by adopting a configuration in which the inside seal part 13 does not seal the outlet-side container 11 it is possible to provide an even greater degree of freedom with respect to arrangement of the outlet port 11a. As a result, an optimal arrangement of elements in which the outlet opening 11c overlaps with the valley part 6 is facilitated.

Figure 5:
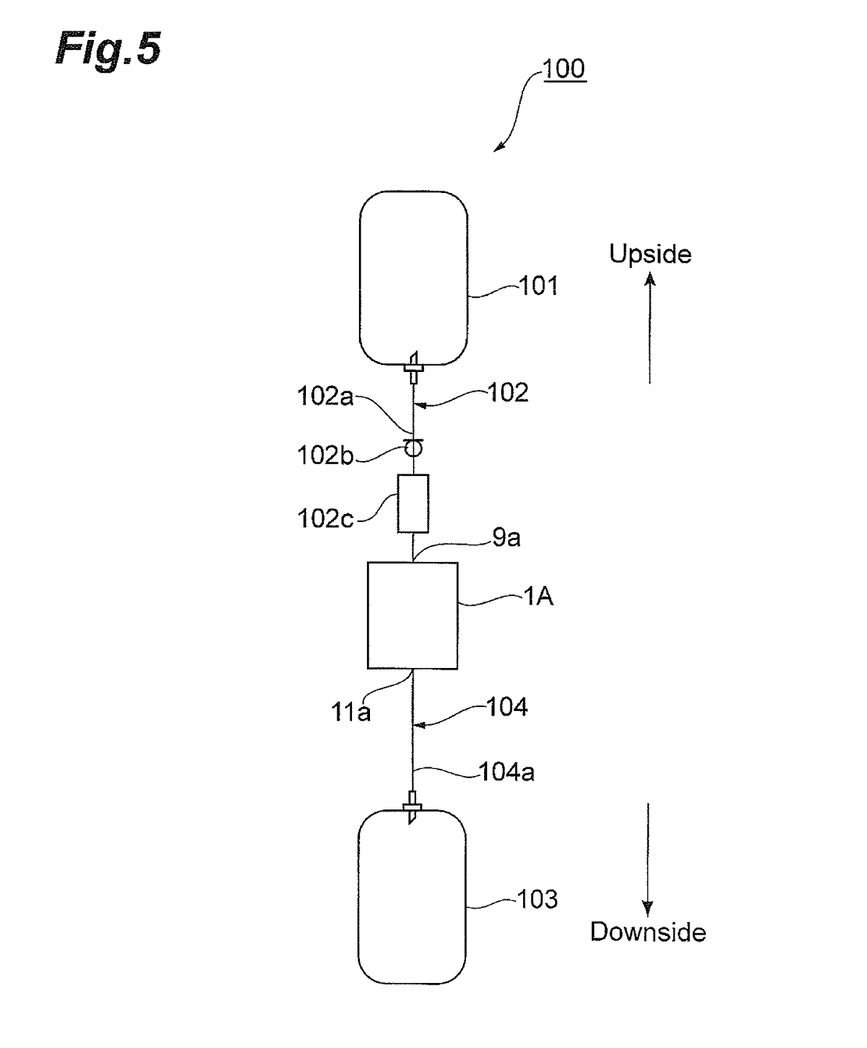
FIG. 5 is a front view that shows an outline of a blood processing system that includes the blood processing filter according to the first embodiment.
Figure 6:
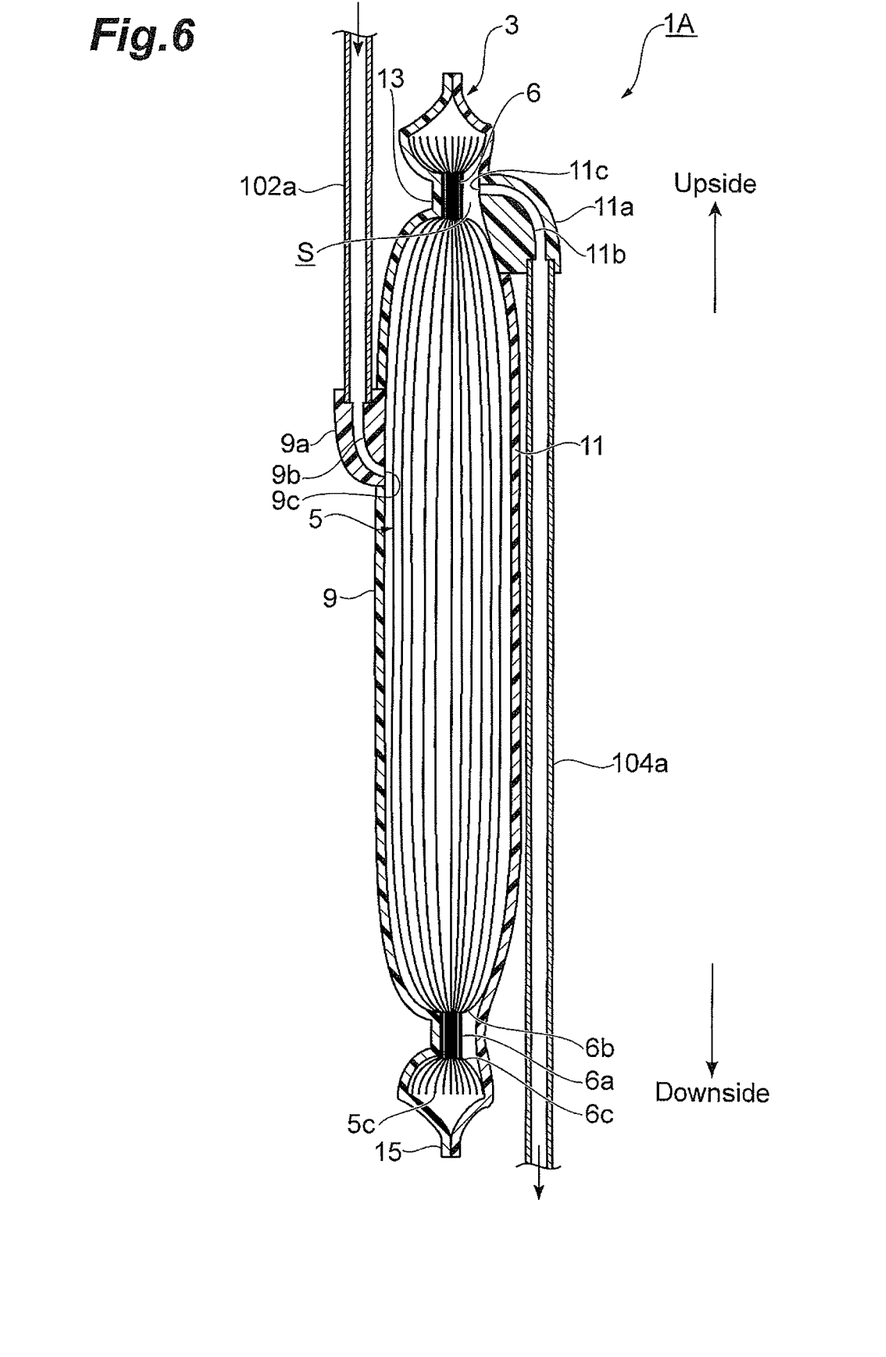
FIG. 6 is a sectional view that illustrates a state when using the blood processing filter according to the first embodiment.

Next, a blood processing system 100 that includes the blood processing filter 1A according to the first embodiment and a usage state (state in which blood is flowing) of the blood processing filter 1A is described referring to FIG. 5 and FIG. 6. FIG. 5 is a front view that illustrates an outline of a blood processing system. FIG. 6 is a sectional view that illustrates a state when the blood processing filter is being used.

The blood processing filter 1A can be used for filtering using gravity. For example, the blood processing system 100 to which the blood processing filter 1A is applied includes a reservoir bag 101 into which blood is filled after collection, the blood processing filter 1A, and a recovery bag 103 for accumulating blood after filtering. The reservoir bag 101 and the inlet port 9a of the blood processing filter 1A are connected to each other by a capillary tube 102a such as a blood tube. The recovery bag 103 and the outlet port 11a of the blood processing filter 1A are connected to each other by a capillary tube 104a such as a blood tube. Further, opening/closing means 102b such as a roller clamp that opens and closes a flow channel and a chamber 102c and the like is mounted in the capillary tube 102a on the upstream side. The inlet-side circuit 102 is formed by the capillary tube 102a, the opening/closing means 102b, and the chamber 102c and the like. The outlet-side circuit 104 is funned by the capillary tube 104a and the like on the downstream side.

The reservoir bag 101 into which blood is filled after collection is arranged at a position that is approximately 50 cm higher than the blood processing filter 1A. The recovery bag 103 in which blood is accumulated after filtering is arranged at a position that is approximately 100 cm lower than the blood processing filter 1A. A blood filtering process is performed by opening the flow channel of the blood processing system 100. When performing the filtering process (at the time of use), a negative pressure arises on the outlet side of the flexible container 3 of the blood processing filter 1A, and the outlet-side container 11 deforms and adheres to the filter element 5. However, the valley part 6 that is recessed with respect to the main region portion 8 is formed on the outlet side of the filter element 5 and, in addition, the outer slanted face portion 6c (protruding nonwoven fabric portion 5c) of the valley part 6 interferes with the outlet-side container 11 so that adherence to the filter element 5 is partially restricted. Therefore, an empty space region (passage region) S is formed by the valley part 6 between the filter element 5 and the outlet-side container 11. Further, since at least one portion of the outlet opening 11c is arranged so as to overlap with the valley part 6, the blood flow channel is stably maintained without being blocked.

Next, the actions and effects of the blood processing filter 1A according to the present embodiment are described. In the blood processing filter 1A, the outlet-side container 11 is not included in the inside seal part 13. As a result, the valley part 6 that is partially recessed is formed in the filter element 5. Further, in the blood processing filter 1A, the passage region S is formed by the valley part 6 in a state in which blood is flowing, and the passage region S is utilized as a blood flow channel (see FIG. 7). In addition, because the valley part 6 is positioned at the periphery of the effective filtering portion 5a of the filter element 5, a flow of blood to the valley part 6 as a blood flow channel from the filter element 5 on the outlet side spreads out and does not concentrate at one point. Accordingly, even if a dual force caused by a positive pressure on the inlet side and a negative pressure on the outlet side acts at the time of filtering, it is possible to avoid a situation in which a flow is inhibited by adherence or the like between the outlet-side container 11 and the filter element 5 and the filtering performance is lowered. This is advantageous in terms of effectively utilizing the entire filter element 5, and thus both a high filtering flow rate and high filtering performance can be achieved in a compatible manner.

Furthermore, according to the blood processing filter 1A of the present embodiment, since at least one portion of the outlet opening 11c of the outlet port 11a is arranged so as to overlap with the valley part 6, the valley part 6 as a blood flow channel and the outlet port 11a are connected and thus blood can be efficiently discharged, and at the same time, a risk of the outlet opening 11c being blocked by the filter element 5 can be eliminated.

Further, according to the blood processing filter 1A of the present embodiment, the outlet opening 11c is provided at a position that is higher than the inlet opening 9c in a state in which the blood processing filter 1A is placed upright to perform blood processing. In particular, the outlet opening 11c is provided at the uppermost position of the region that overlaps with the valley part 6. As a result, more complete air removal and priming can be achieved, and a pressure difference between the inlet side and the outlet side during filtration can be minimized.

The advantages of the blood processing filter 1A and the method for manufacturing the blood processing filter 1A of the present embodiment will now be summarized. According to the blood processing filter 1A, the passage region S formed by the valley part 6 on the outlet side of the flexible container 3 can be utilized as a blood flow channel without leading to the risk of a welding defect, complicating the manufacturing process, or increasing costs. As a result, a situation in which the flow of blood is inhibited and filtering performance declines can be avoided, more complete priming and air removal can be realized, the entire filter element 5 can be effectively utilized, and a high flow rate and high filtering performance can be simultaneously achieved. Further, the blood processing filter 1A that provides such advantages can be manufactured.

Figure 8:
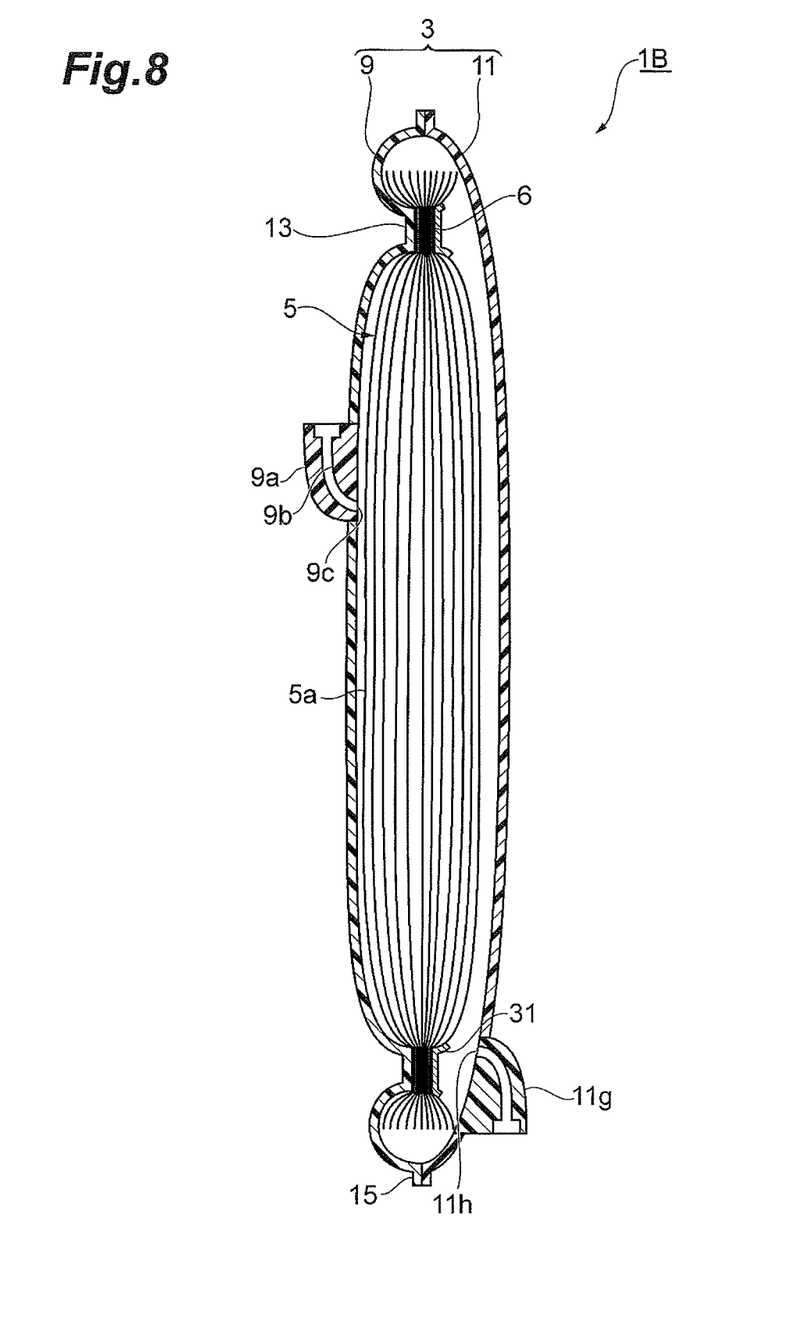
FIG. 8 is a sectional view of a blood processing filter according to a second embodiment of the present invention.
Figure 9:
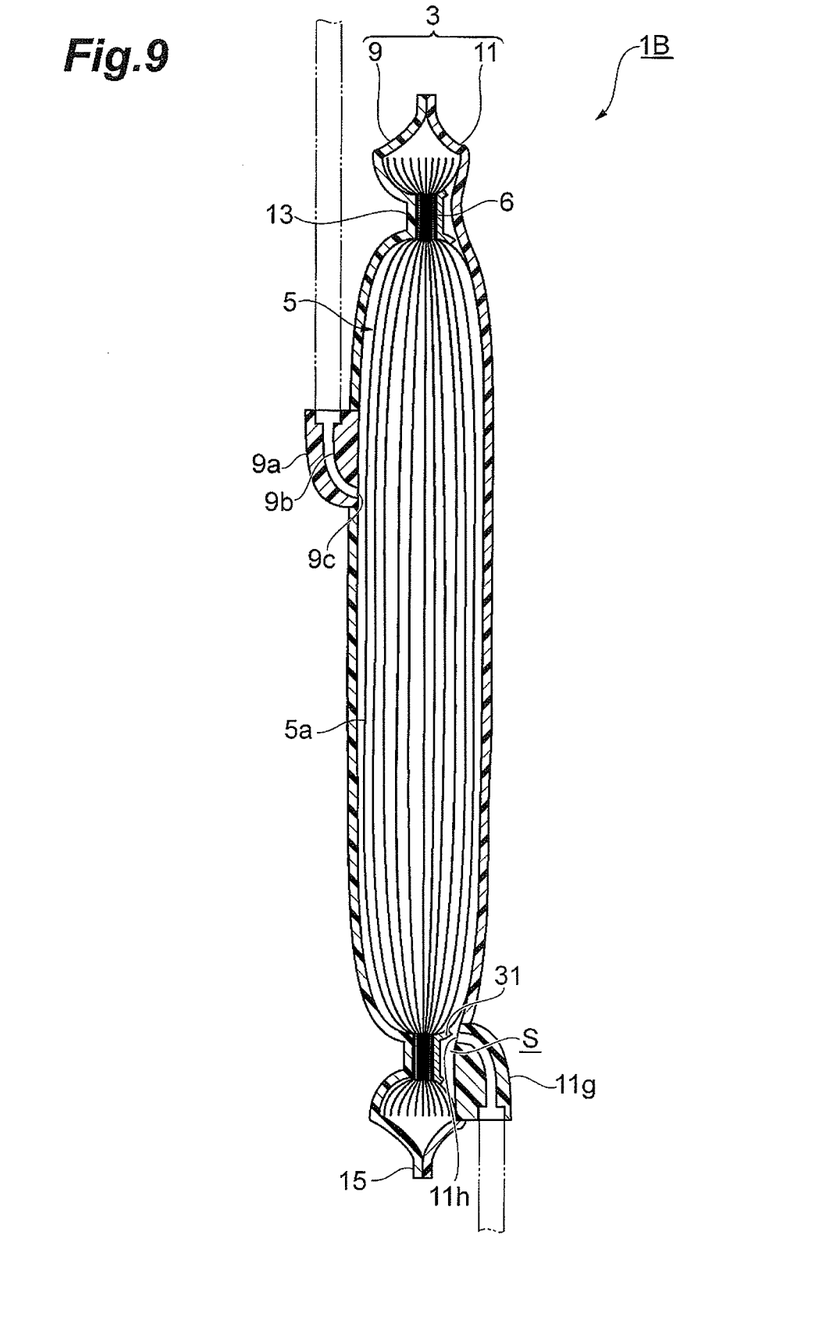
FIG. 9 is a sectional view that illustrates a state when using the blood processing filter according to the second embodiment.

Next, a blood processing filter according to a second embodiment of the present invention is described referring to FIG. 8 and FIG. 9. FIG. 8 is a sectional view of the blood processing filter according to the second embodiment of the present invention. FIG. 9 is a sectional view that illustrates a state when using the blood processing filter according to the second embodiment. In this connection, a blood processing filter 1B according to the second embodiment includes substantially the same elements and structures as the blood processing filter 1A according to the first embodiment. Hence, elements and structures that are the same as in the first embodiment are denoted by the same reference symbols and a detailed description thereof is omitted, and the following description centers on elements and structures that are different from those of the first embodiment.

The blood processing filter 1B includes a flexible container 3 that has an inlet port 9a and an outlet port 11g for blood, a sheet-like filter element 5 that is arranged so as to divide the inside of the flexible container 3 into an inlet port 9a side and an outlet port 11g side, and a welding sheet 31 that is arranged on the outlet side of the filter element 5 at a position that corresponds to a position at which the inside seal part 13 is formed. The flexible container 3 includes an inlet-side container 9 having a rectangular sheet shape, and an outlet-side container 11 having a rectangular sheet shape.

The inlet-side container 9 and the outlet-side container 11 overlap with each other through the rectangular filter element 5. The inlet-side container 9, the filter element 5, and the welding sheet 31 are adhered to each other and sealed, and as a result a band-shaped inside seal part 13 is formed along the periphery of the filter element 5. The valley part 6 is formed in the filter element 5 by the inside seal part 13, and in a state in which blood is flowing (state at a time of use), a passage region S is formed between the valley part 6 and the outlet-side container 11.

An outlet port 11g of the present embodiment is arranged at a position that is on a lower side of the blood processing filter 1B in a state in which the blood processing filter 1B is upright to perform blood processing, more specifically, at a position that is below the inlet port 9a when filtration is performed by means of a gravity drop. At least one portion of the outlet opening 11h is arranged so as to overlap with the valley part 6.

According to the blood processing filter 1B of the present embodiment, even if a dual force generated by a positive pressure on the inlet side and a negative pressure on the outlet side acts at the time of filtering, it is possible to avoid a situation in which the blood flow is inhibited by adherence or the like between the outlet-side container 11 and the filter element 5 and filtering performance is lowered. This is advantageous in terms of effectively utilizing the entire filter element 5, and thus both a high filtering flow rate and high filtering performance can be achieved in a compatible manner.

EXAMPLES

The present invention will now be described in further detail below by way of examples. However, the following examples should not be construed as limiting the present invention.

Example 1

A filter including an inlet-side container (inlet-side flexible container), an outlet-side container (outlet-side flexible container) and a filter element was prepared, and an inlet port thereof was connected to a pre-filtration liquid reservoir bag via an inlet-side circuit having a length of 50 cm. An outlet port of the filter was connected to a post-filtration liquid recovery bag via an outlet-side circuit having a length of 100 cm. A tube made of soft polyvinyl chloride having an internal diameter of 2.9 mm and an external diameter of 4.2 mm was used for the inlet-side circuit and the outlet-side circuit.

In preparing the filter, an effective filtering portion was formed in a rectangular shape in which an inner side of an inside seal part (first seal part) had a longitudinal dimension of 74 cm and a horizontal dimension of 57 cm, a corner portion was formed as a curve, and an effective filtration area of $42 \times 10^{-4}$ ($m^2$) was provided. As the filter element, four sheets of polyester nonwoven fabric having an air permeability of 237.3 ($cc/cm^2/sec$) and a thickness of 0.2 mm, one sheet of polyester nonwoven fabric having an air permeability of 8.4 ($cc/cm^2/sec$) and a thickness of 0.4 mm, 32 sheets of polyester nonwoven fabric having an air permeability of 7.7 ($cc/cm^2/sec$) and a thickness of 0.20 mm, one sheet of nonwoven polyester fabric having an air permeability of 8.4 ($cc/cm^2/sec$) and a thickness of 0.4 mm, and four sheets of nonwoven polyester fabric having an air permeability of 237.3 ($cc/cm^2/sec$) and a thickness of 0.2 mm were stacked in that order from an inlet to an outlet at the time of filtering blood, and used. In this connection, the air permeability was measured by a method based on Japanese Industrial Standard JIS L-1096, 6.27.1A.

The inlet port and outlet port were sealed to the inlet-side flexible container and the outlet-side flexible container, respectively. The first seal part was formed by disposing the inlet-side flexible container and the filter element in a layered arrangement, and thereafter the second seal part was formed by overlaying the outlet-side flexible container thereon. At that time, sealing and assembly were performed so as to provide an inlet opening for allowing blood to flow out from the inlet port to inside the inlet-side flexible container at a position that was 2.4 cm below an end on the effective filtering portion side of the uppermost portion of the first seal part (valley part). Further, sealing and assembly were performed so that an outlet opening for allowing blood to flow out from inside the outlet-side flexible container to an outlet port overlapped with the lowermost portion of the first seal part (valley part).

The total of the upstream side drop, the drop between the inlet and outlet of the filter, and the downstream side drop was fixed at 150 cm. Thereafter, as a liquid to be processed (a blood substitute), 300 g of an aqueous solution of polyvinyl pyrrolidone (molecular weight: 360,000) adjusted to a viscosity of 17 mPa·s (25° C.) and pH 3.8 was filled into a pre-filtration liquid reservoir bag, and caused to flow at room temperature using gravity. A post-filtration liquid recovery bag was placed in advance on a scale balance to enable verification of changes in the weight thereof.

At this time, the time required from when the liquid to be processed started to flow until the liquid first reached the inlet of the post-filtration liquid recovery bag was measured, and the measured time was defined as a priming time (minutes). Further, a time required from when the liquid to be processed started to flow until all of the liquid to be processed was discharged from inside the pre-filtration liquid reservoir bag and a converted weight of the post-filtration liquid recovery bag ceased to increase, more specifically, the time required to filter all of the liquid, was measured, and the measured time was defined as a total processing time (minutes). The weight of the liquid recovered in the post-filtration liquid recovery bag was measured and defined as a recovery amount (g). A mean processing speed (g/min) was determined by calculation based on the recovery amount and the total processing time. A difference between the 300 g of liquid that was filled into the pre-filtration liquid reservoir bag and the recovery amount was determined by calculation, and defined as a loss amount (g).

Example 2

Filtering was carried out using a filter assembled by the same method as in Example 1, except that sealing and assembly were performed so that the outlet opening of the outlet port overlapped with the uppermost portion of the first seal part (valley part).

Comparative Example 1

Filtering was carried out using a filter assembled by the same method as in Example 1, except that sealing and assembly were performed so that the outlet opening of the outlet port was provided at a position that was 2.4 cm above an end on the effective filtering portion side of the lowermost portion of the first seal part.

Comparative Example 2

Filtering was carried out using a filter assembled by the same method as in Comparative Example 1, except that a first seal part was formed by disposing the inlet-side flexible container, the filter element, and the outlet-side flexible container in a layered arrangement, and thereafter the second seal part was formed.

Table 1 shows a summary of the results of Examples 1 and 2, and Comparative Examples 1 and 2.

TABLE 1

|  | Example 1 | Example 2 | Comparative Example 1 | Comparative Example 2 |
|---|---|---|---|---|
| Priming Time (min) | 2.5 | 4.7 | 2.8 | 2.3 |
| Total Processing Time (min) | 23.7 | 19.6 | 26.1 | 26.4 |
| Recovery amount (g) | 258.7 | 257.8 | 258.3 | 260.9 |
| Mean Processing Speed (g/min) | 10.9 | 13.2 | 9.9 | 9.9 |
| Loss Amount (g) | 41.3 | 42.2 | 41.7 | 39.1 |

The results showed that, for Example 1, the total processing time is shortened and the mean processing speed is improved compared to Comparative Example 1. This is because, irrespective of the fact that the outlet port in Example 1 is provided at a lower position than in Comparative Example 1, because the position of the outlet port in Example 1 is over the first seal part (valley part), blood that passes through the effective filtering portion does not concentrate at one point of the outlet port, but rather, can flow temporarily in diffuse directions towards the first seal part that is on the outer side of the effective filtering portion, flow through the valley part corresponding to the first seal part as a flow channel, and flow towards the outlet opening of the outlet port that is connected to the aforementioned flow channel.

The results showed that the priming time increased in Example 2. However, this is not a substantial extension of the priming time, but rather relates to the fact that the outlet port is disposed at the upper portion of the filter in order to carry out more complete priming and air removal. More specifically, the priming time increases because liquid is not discharged to outside the filter during priming, and hence the outlet side of the filter fills with liquid. Once liquid starts to flow out from the filter and the outlet-side circuit fills with liquid, the liquid accumulated on the outlet side of the filter is rapidly discharged to outside the filter by a negative pressure. Accordingly, the apparent extension in the priming time does not extend the total processing time.

The shortest total processing time was obtained using the filter of Example 2. This is because, as the result of performing complete air removal and priming, the filter element at the effective filtering portion is not blocked by residual air and is completely filled with the liquid, and furthermore, because the outlet port (outlet opening) is arranged at a higher position than the inlet port (inlet opening), a pressure difference between the inlet side and the outlet side of the filter is suppressed to a minimum and attachment between the outlet-side flexible container and the filter element is reduced. That is, the total processing time is shorter because the filter element is effectively utilized.

What is claimed is:

1. A blood processing filter comprising a sheet-like filter element, an inlet-side flexible container and an outlet-side flexible container that sandwich the filter element and are sealed thereto, an inlet port provided in the inlet-side flexible container for accepting blood before being processed by the filter element, and an outlet port provided in the outlet-side flexible container for discharging blood after being processed by the filter element;

the blood processing filter further comprising:
a band-shaped first seal part that seals the inlet-side flexible container and the filter element so as to surround the inlet port; and
an annular second seal part that seals at least the inlet-side flexible container and the outlet-side flexible container, and that is formed so as to surround the first seal part at a position that is closer to an outer edge than the first seal part;
wherein:
a valley part corresponding to the first seal part is provided on an outlet side of the filter element;
an outlet opening that communicates with an inside of the outlet-side flexible container is formed in the outlet port;
at least one portion of the outlet opening is arranged so as to overlap with the valley part, and
the outlet side flexible container is formed so as not to be adhered to the filter element by the first seal part.

2. The blood processing filter according to claim 1, wherein:
an inlet opening that communicates with an inside of the inlet-side flexible container is formed in the inlet port; and
the outlet opening is provided at a position that is higher than the inlet opening in a state in which the blood processing filter is placed upright to perform blood processing.

3. The blood processing filter according to claim 1, wherein the outlet opening is provided at an uppermost position of a region that overlaps with the valley part in a state which the blood processing filter is placed upright to perform blood processing.

4. A method for manufacturing a blood processing filter comprising a sheet-like filter element, an inlet-side flexible container and an outlet-side flexible container that sandwich the filter element and are sealed thereto, an inlet port provided in the inlet-side flexible container for accepting blood before being processed by the filter element, and an outlet port provided in the outlet-side flexible container for discharging blood after being processed by the filter element;

the method comprising:
an installing step of arranging the inlet-side flexible container and the outlet-side flexible container so as to sandwich the filter element;
a first sealing step of forming a band-shaped first seal part by sealing the inlet-side flexible container and the filter element so as to surround an area where the inlet port is formed, without adhering the filter element and the outlet-side flexible container; and
a second sealing step of forming an annular second seal part by sealing so as to surround the first seal part at a position that is closer to an outer edge than the first seal part;

wherein:
a band-shaped valley part that corresponds to the first seal part is generated on an outlet side of the filter element by the first sealing step;
an outlet opening that communicates with an inside of the outlet-side flexible container is formed in the outlet port; and
at least one portion of the outlet opening is formed so as to overlap with the valley part.

5. The method for manufacturing a blood processing filter according to claim 4, wherein:
an inlet opening that communicates with an inside of the inlet-side flexible container is formed in the inlet port; and
the outlet opening of the outlet port is provided at a position that is higher than the inlet opening of the inlet port in a state in which the blood processing filter is placed upright to perform blood processing.

6. The method for manufacturing a blood processing filter according to claim 4, wherein the outlet opening of the outlet port is provided at an uppermost position of a region that overlaps with the valley part in a state which the blood processing filter is placed upright to perform blood processing.

\* \* \* \* \*